(12) United States Patent
Polsinelli

(10) Patent No.: US 7,755,071 B2
(45) Date of Patent: Jul. 13, 2010

(54) LEAK RESISTANT SYRINGE COVER

(76) Inventor: Perry Polsinelli, 4150 Waterford Dr., Suwanee, GA (US) 30024

( * ) Notice: Subject to any disclaimer, the term of this patent is extended or adjusted under 35 U.S.C. 154(b) by 211 days.

(21) Appl. No.: 11/856,300

(22) Filed: Sep. 17, 2007

(65) Prior Publication Data

US 2009/0072169 A1   Mar. 19, 2009

(51) Int. Cl.
*G21F 5/00* (2006.01)
*B65D 85/24* (2006.01)

(52) U.S. Cl. ............ 250/519.1; 250/505.1; 250/506.1; 250/515.1; 600/5; 604/193; 604/194; 206/364; 206/365

(58) Field of Classification Search ............ 600/1, 600/3, 4, 5, 7; 604/212, 213, 217, 218, 239, 604/257, 187, 197, 199, 299, 193, 194; 250/505.1, 250/506.1, 507.1, 515.1, 519.1; 206/349, 206/364, 365, 305
See application file for complete search history.

(56) References Cited

U.S. PATENT DOCUMENTS

| | | | | |
|---|---|---|---|---|
| 4,433,974 A | * | 2/1984 | Bischof | 604/407 |
| 4,880,413 A | * | 11/1989 | Giuffre et al. | 604/192 |
| 5,332,092 A | * | 7/1994 | Fischer | 206/365 |
| 5,725,501 A | * | 3/1998 | Lichtenberg | 604/110 |
| 5,989,229 A | * | 11/1999 | Chiappetta | 604/263 |
| 5,993,426 A | * | 11/1999 | Hollister | 604/192 |
| 2001/0021820 A1 | * | 9/2001 | Lynn | 604/90 |
| 2002/0103471 A1 | * | 8/2002 | Granier | 604/506 |
| 2003/0181862 A1 | * | 9/2003 | Lin | 604/198 |
| 2003/0222228 A1 | * | 12/2003 | Chen Fu et al. | 250/507.1 |

* cited by examiner

*Primary Examiner*—Jack I Berman
*Assistant Examiner*—Nicole Ippolito Rausch
(74) *Attorney, Agent, or Firm*—Bryan W. Bockhop; Bockhop & Associates, LLC

(57) ABSTRACT

A cover for a syringe includes an elongated flexible envelope and an absorbent material. The elongated flexible envelope includes a body portion and a needle-receiving portion. The body portion has a first end that defines an opening and an opposite second end. The needle-receiving portion extends from the second end of the body portion and terminates in a distal end. The body portion and the needle-receiving portion define a cavity of sufficient size to allow the syringe to be placed therein. The cavity is in communication with the opening. The envelope is made of a material that is impervious to liquid. The absorbent material is disposed in the distal end of the needle-receiving portion.

22 Claims, 1 Drawing Sheet

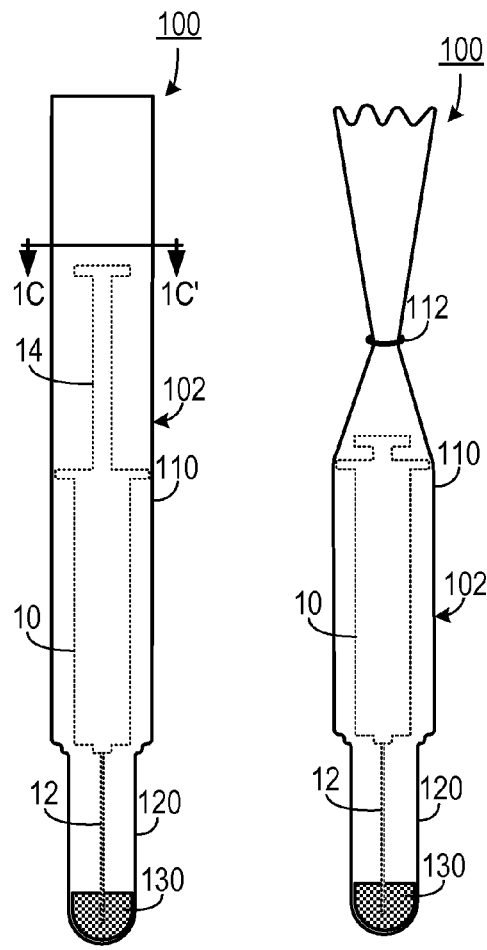
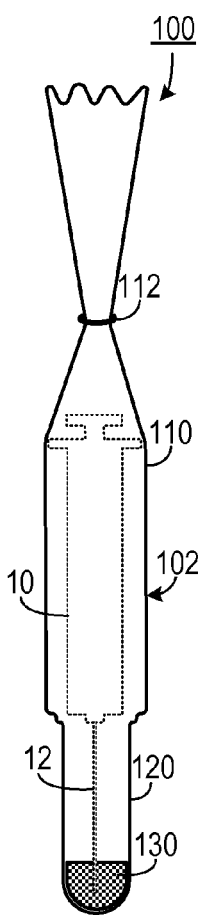
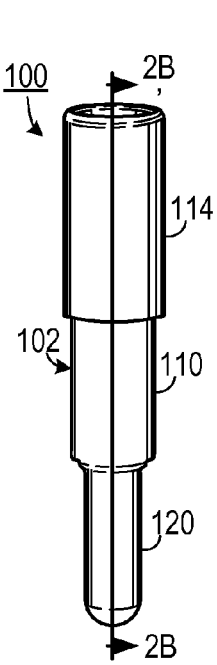
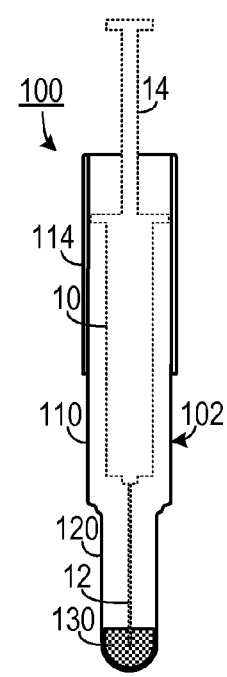
FIG. 1A  FIG. 1B
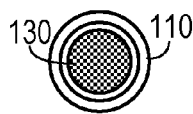
FIG. 1C
FIG. 2A  FIG. 2B
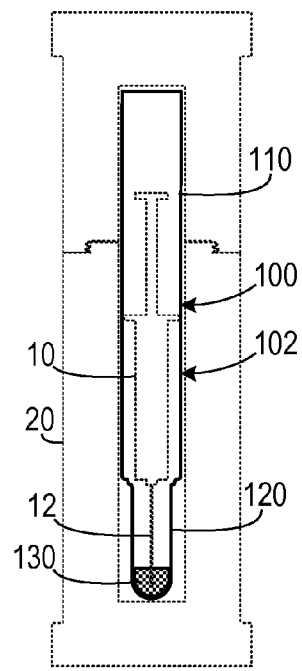
FIG. 3

LEAK RESISTANT SYRINGE COVER

BACKGROUND OF THE INVENTION

1. Field of the Invention

The present invention relates to medical devices and, more specifically, to a devise for containing leakage from a syringe.

2. Description of the Prior Art

Syringes are commonly used by health care professionals for delivering pharmaceutical substances and receiving bodily fluids. Some syringes are used to deliver substances that can be harmful is one is exposed to them outside the context of their intended medical use. For example, radio-pharmaceutical liquids can be harmful to those administering the liquids if they fail to handle the liquids properly.

Syringes that contain radio-pharmaceutical liquids are often placed in reusable pigs, which are devices made from shielding material that prevent radiation from the liquids from entering the surrounding areas during handling. Once a syringe is used, it is often placed back into the pig. Such a syringe may contain harmful fluids, which may leak into to pig. Since the pig is reusable, the leakage of harmful fluids into the pig requires extra cleaning of a hazardous substance. Also, since the syringe could contain microbes, such leakage could lead to the propagation of harmful microbes.

Therefore, there is a need for a syringe cover that prevents leakage of harmful liquids.

SUMMARY OF THE INVENTION

The disadvantages of the prior art are overcome by the present invention which, in one aspect, is a cover for a syringe that includes an elongated flexible envelope and an absorbent material. The elongated flexible envelope includes a body portion and a needle-receiving portion. The body portion has a first end that defines an opening and an opposite second end. The needle-receiving portion extends from the second end of the body portion and terminates in a distal end. The body portion and the needle-receiving portion define a cavity of sufficient size to allow the syringe to be placed therein. The cavity is in communication with the opening. The envelope is made of a material that is impervious to liquid. The absorbent material is disposed in the distal end of the needle-receiving portion.

In another aspect, the invention is a cover for a syringe that includes an elongated flexible envelope, an absorbent material and a substance that prevents growth of a predetermined set of microorganisms absorbed into the absorbent material.

In yet another aspect, the invention is a method of making a syringe cover, in which an elongated envelope is formed from a flexible material that is impervious to liquid so that the envelope includes a body portion and a needle-receiving portion, terminating in a distal end, and so that envelope defines a cavity that is configured to receive a syringe therein. An absorbent material is disposed adjacent to the distal end.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIG. 1A is a cross sectional view of one embodiment.

FIG. 1B is a cross sectional view of the embodiment shown in FIG. 1A that is configured to seal a used syringe therein.

FIG. 1C is a cross sectional view of the embodiment shown in FIG. 1A, taken along line 1C-1C'.

FIG. 2A is a top perspective view of one embodiment configured with a cuff.

FIG. 2B is a cross sectional view of the embodiment shown in FIG. 2A, taken along line 2B-2B'.

FIG. 3 is a cross sectional view of an embodiment disposed in a radio pharmaceutical pig.

DETAILED DESCRIPTION OF THE INVENTION

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIGS. 1A-1B, one embodiment of the invention is a cover 100 for a syringe 10 that includes an elongated flexible envelope 102 (which could include, e.g., a latex material or a synthetic rubber) that includes a body portion 110, which is shaped to receive the body of the syringe 10 therein, and a needle-receiving portion 120, which is shaped to receive a syringe needle 12 therein. An absorbent material 130 is placed in the end of the needle-receiving portion 120. The absorbent material 130 could include a synthetic sponge material and other liquid-absorbing materials (e.g., a sodium polyacrylate). When the needle 12 is stuck in the absorbent material 130, any liquids leaking out of the needle 12 are absorbed and stabilized by the absorbent material 130. Addition of a material such as a disinfectant, a bactericide, a fungicide or an antiseptic to the absorbent material 130 will further reduce the likelihood of growth of harmful microorganisms.

The envelope 102 may have a length that is longer that the syringe 12 when the syringe 10 has an extended plunger 14. Once the syringe 10 is used, it is placed into the elongated flexible envelope 102 so that the needle 12 sticks into the absorbent material 130 and the flexible envelope 102 is sealed with a sealing device 112 such as a rubber band, or the end is simply tied in a knot.

As shown in FIGS. 2A-2B, a portion of the body portion 110 can be folded over to form a cuff 114 so that a portion of the syringe 10 is allowed to to stick out of the top opening of the body portion 110. This provides ready access to the syringe 10.

As shown in FIG. 3, the cover 100 is complimentary in shape to the inside of a radio-pharmaceutical pig 20, to allow easy placement therein.

The cover 100 may be made using well known techniques for forming latex devices. Similarly, the absorbent material 130 may be placed into the cover 100 using well known assembly techniques.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A cover for a syringe, comprising:
   a. an elongated flexible envelope that includes a body portion and a needle-receiving portion, the body portion having a first end that defines an opening and an opposite second end, the needle-receiving portion extending from the second end of the body portion and terminating in a distal end, the body portion and the needle-receiving portion defining a cavity of sufficient size to allow the syringe to be placed therein, the cavity in communication with the opening, the envelope being made of a material that is impervious to liquid; and
   b. an absorbent material disposed in the distal end of the needle-receiving portion.

2. The cover of claim 1, disposed in a radio pharmaceutical pig.

3. The cover of claim 1, wherein the envelope has a length that is longer than the syringe when the syringe has an extended plunger.

4. The cover of claim 1, wherein the envelope has a length so that a portion of the body portion extends beyond the syringe, thereby allowing the opening to be sealed with the syringe disposed therein.

5. The cover of claim 1, wherein the envelope comprises a latex material.

6. The cover of claim 1, wherein the absorbent material comprises a synthetic sponge material.

7. The cover of claim 1, wherein the absorbent material includes a substance that prevents growth of a predetermined set of microorganisms.

8. The cover of claim 7, wherein the substance includes a material selected from a group consisting essentially of: a disinfectant, a bactericide, a fungicide and an antiseptic, and combinations thereof 9. The cover of claim 1, wherein the envelope has an external shape that allows the cover to be placed in a pig for radiopharmaceuticals.

10. The cover of claim 1, wherein a portion of the body portion forms a cuff, the cuff having a length that allows a portion of the syringe to stick out of the opening, the cuff being folded downwardly over a portion of the body portion and configured to be unfolded so that the portion of the body portion that forms a cuff will extend above the syringe so as to facilitate sealing of the syringe within the cover.

11. A cover for a syringe, comprising:
   a. an elongated flexible envelope that includes a body portion and a needle-receiving portion, the body portion having a first end that defines an opening and an opposite second end, the needle-receiving portion extending from the second end of the body portion and terminating in a distal end, the body portion and the needle-receiving portion defining a cavity of sufficient size to allow the syringe to be placed therein, the cavity in communication with the opening, the envelope being made of a material that is impervious to liquid, a portion of the body portion forming a cuff that has a length that allows a portion of the syringe to stick out of the opening, the cuff being folded downwardly over a s portion of the body portion and configured to be unfolded so that the portion of the body portion that forms a cuff will extend above the syringe so as to facilitate sealing of the syringe within the cover;
   b. an absorbent material disposed in the distal end of the needle-receiving portion; and
   c. a substance that prevents growth of a predetermined set of microorganisms absorbed into the absorbent material.

12. The cover of claim 11, wherein the envelope has a length that is longer than the syringe when the syringe has an extended plunger.

13. The cover of claim 11, wherein the envelope has a length so that a portion of the body portion extends beyond the syringe, thereby allowing the opening to be sealed with the syringe disposed therein.

14. The cover of claim 11, wherein the envelope comprises a latex material.

15. The cover of claim 11, wherein the absorbent material comprises a synthetic sponge material.

16. The cover of claim 11, wherein the substance includes a material selected from a group consisting essentially of: a disinfectant, a bactericide, a fungicide and an antiseptic, and combinations thereof.

17. The cover of claim 11, wherein the envelope has an external shape that allows the cover to be placed in a pig for radiopharmaceuticals.

18. The cover of claim 11, further comprising a radio pharmaceutical pig into which the envelope is placed.

19. A method of making a syringe cover, comprising the steps of:
   a. forming an elongated envelope from a flexible material that is impervious to liquid so that the envelope includes a body portion and a needle-receiving portion, terminating in a distal end, and so that envelope defines a cavity that is configured to receive a syringe therein; and
   b. disposing an absorbent material adjacent to the distal end.

20. The method of claim 19, further comprising the step of placing an anti-microbial agent in the absorbent material.

21. The method of claim 20, wherein the anti-microbial substance includes a material selected from a group consisting essentially of: a disinfectant, a bactericide, a fungicide and an antiseptic, and combinations thereof 22. The method of claim 19, wherein the step of disposing an absorbent material comprises the step of placing a sponge material in the cavity adjacent to the distal end.

* * * * *